United States Patent

Suzuki

Patent Number: 5,323,111
Date of Patent: Jun. 21, 1994

[54] MAGNETIC RESONANCE IMAGING METHOD AND APPARATUS

[75] Inventor: Katsunori Suzuki, Abiko, Japan

[73] Assignee: Hitachi Medical Corp., Tokyo, Japan

[21] Appl. No.: 29,601

[22] Filed: Mar. 11, 1993

[30] Foreign Application Priority Data

Mar. 11, 1992 [JP] Japan .................................. 4-052154

[51] Int. Cl.[5] .............................................. G01V 3/00
[52] U.S. Cl. .................................................... 324/309
[58] Field of Search ............... 324/300, 307, 309, 310, 324/311, 312, 313, 314, 318, 322; 128/653.2, 653.5

[56] References Cited

U.S. PATENT DOCUMENTS

| | | | |
|---|---|---|---|
| 4,422,042 | 12/1983 | Sugimoto | 324/313 |
| 4,831,329 | 5/1989 | Hughes | 324/309 |
| 5,206,593 | 4/1993 | Kurihara et al. | 324/312 |

*Primary Examiner*—Michael J. Tokar
*Attorney, Agent, or Firm*—Antonelli, Terry, Stout & Kraus

[57] ABSTRACT

A first sectional image corresponding to a first section of an object to be examined is displayed on a screen of a display device. A position of a first line on the first sectional image is designated. First data corresponding to a distance between the first line and a center of the screen is obtained. A second sectional image corresponding to a second section of the object is displayed on the screen. The second section crosses the first section on a line on the first section corresponding to the position of the first line. A position of a second line on the second sectional image is designated. A position of a first point contained in the position of the second line is designated. Second data corresponding to a component in the direction of the second line is obtained. The component is a component of the distance between the first point and the center of the screen. A third sectional image corresponding to a third section of the object, is displayed on the screen on the basis of the first and second data in such a way that a point on the third sectional image corresponding to a point on the third section. The third section crosses the second section on a line on the second section corresponding to the position of the second line. The point on the third section is specified by both of the first line and the first point is displayed at a substantial center of the screen.

7 Claims, 6 Drawing Sheets

MAGNETIC RESONANCE IMAGING METHOD AND APPARATUS

BACKGROUND OF THE INVENTION

This invention relates to a magnetic resonance imaging method and apparatus.

The following procedure is employed in a conventional magnetic resonance imaging apparatus to obtain a sectional image corresponding to a desired section of an object to be examined.

First of all, a so-called "scout view" as a sectional image along a body axis of an object to be examined is displayed on a screen of a display device. Line cursors representing a slice portion in this scout view are moved and a sectional image sliced at a desired cursor position is displayed on the screen. The line cursors representing the slice portion of this sectional image are further moved, and a sectional image sliced at a desired cursor position is displayed on the screen.

The sectional image finally obtained in this way is an image along each line cursor, that is, an image of a section sliced on a plane required by an operator.

However, the sectional image finally obtained is displayed in some cases a little to the right or left of the center on the screen of the display device depending on the position of the object inside a gantry.

Therefore, according to the prior art, a point cursor capable of moving along the line cursor is also displayed in superposition with the line cursor, which is in turn displayed in superposition with a sectional view to be displayed next to the scout view, and this point cursor is positioned to a predetermined position of the sectional image so that a final sectional image can be displayed while the portion of this point cursor thus positioned is in agreement with the center of the screen in the horizontal direction.

In the magnetic resonance imaging apparatus having the construction as described above, however, the sectional image is so displayed as to be positioned to the center of the screen in the horizontal direction, but positioning in the vertical direction of the screen has not been taken into consideration. Accordingly, a desired sectional image (final sectional image) is displayed a little upward or downward on the screen depending on the position of the object inside the gantry.

To solve this problem, an imaging technique has been proposed recently which first displays a sectional image (the final sectional image described above) positioned a little upward or downward, displays then the point cursor in superposition with this sectional image, and positions the point cursor to a predetermined portion so that the predetermined portion can be positioned to the center of the screen in the vertical direction and the desired image can be displayed.

However, this technique invites another problem that the number of sectional images to be displayed at a preliminary stage must be increased by one so as to obtain or designate a desired sectional image, and the procedure becomes too much complicated.

SUMMARY OF THE INVENTION

It is an object of the present invention to provide a magnetic resonance imaging method and apparatus capable of displaying a desired sectional image at the center of a screen not only in a horizontal direction but also in a vertical direction of the screen without increasing the number of sectional images to be displayed as a preliminary stage for obtaining or designating the desired sectional image.

To accomplish the object described above, a magnetic resonance imaging method according to an aspect of the present invention includes the steps of: displaying a first sectional image corresponding to a first section of an object to be examined on a screen of a display device; designating a position of a first line on the first sectional image; obtaining first data corresponding to a distance between the first line and a center of the screen; displaying, on the screen, a second sectional image corresponding to a second section of the object, the second section crossing the first section on a line on the first section corresponding to the position of the first line; designating a position of a second line on the second sectional image; designating a position of a first point contained in the position of the second line; obtaining second data corresponding to a component in a direction of the second line, the component being a compornent of the distance between the position of the first point and the center of the screen; and displaying, on the screen, a third sectional image corresponding to a third section of the object on the basis of the first and second data, so that a point on the third sectional image corresponding to a point on the third section is displayed at a substantial center of the screen, the third section crossing the second section on a line on the second section corresponding to the position of the second line, and the point of the third section being specified by both of the first line and the first point.

According to this magnetic resonance imaging method, a sectional image which is displayed as a preliminary state for obtaining the third sectional image as the desired sectional image is the first and second sectional images. Therefore, the number of the sectional images to be displayed at the preliminary stage need not be increased from the number in the prior art. Moreover, since the first and second data described above are utilized, the third sectional image as the desired sectional image can be displayed at the center of the screen.

The step of displaying the first sectional image on the screen described above may include the steps of: obtaining a first NMR signal corresponding to the first section; obtaining first image data corresponding to the first section on the basis of the first NMR signal; and displaying the first sectonal image on the screen on the basis of the first image data.

The step of displaying the second sectional image on the screen described above may include the steps of: obtaining a second NMR signal corresponding to the second section; obtaining second image data corresponding to the second section on the basis of the second NMR signal; and displaying the second sectional image on the screen on the basis of the second image data.

The step of displaying the third sectional image on the screen described above may include the steps of: obtaining a third NMR signal corresponding to the third section of the object crossing the second section on the line on the second section, which in turn corresponds to the position of the second line; performing quadrature phase detection as to the third NMR signal with a detection frequency determined on the basis of the first and second data; performing phase rotation calculation or computation, for rotating a phase of the third NMR signal subjected to the quadrature phase detection, by a phase angle determined on the basis of the first and second data; obtaining the third image data corresponding to the third section on the basis of the third NMR signal subjected to the phase rotation calculation or computation; and displaying the third secional image on the screen on the basis of the third image data.

In this case, quadrature phase detection is performed with the detection frequency determined on the basis of the first and second data, and phase rotation calculation is performed for rotating the phase by the phase angle determined on the basis of the first and second data. Accordingly, even when the position of the object to be examined deviates relatively greatly inside the gantry, a part of the sectional image does not fall off but the entire third sectional image can be displayed.

In another apsect of the present invention, there is provided a magnetic resonance imaging apparatus including: a display unit having a screen, for displaying an image on the screen; a unit for obtaining first image data corresponding to a first section of an object to be examined; a first display control unit for controlling the display unit so that a first sectional image corresponding to the first image data is displayed on the screen; a unit for designating the position of a first line on the first sectional image; a unit for obtaining first data corresponding to a distance between the first line and the center of the screen; a unit for obtaining second image data corresponding to a second section of the object, in which the second section crosses the first sectioin on a line on the first section corresponding to the position of the first line; a second display control unit for controlling the display unit so that a first sectional image corresponding to the second image is displayed on the screen; a unit for designating a position of a second line on the second sectional image; a unit for designating a position of a first point contained in the position of the second line; a unit for obtaining second data corresponding to a component in a direction of the second line, the component being a comporment of the distance between the position of the first point and the center of the screen; a unit for obtaining a third NMR signal corresponding to the third section of the object, in which the third section crosses the second section on a line on the second section corresponding to the position of the second line; a unit for performing quadrature phase detection as to the third NMR signal with a detection frequency determined on the basis of the first and second data; a unit for performing phase rotation calculation, for rotating a phase by a phase angle determined on the basis of the first and second data, as to the third NMR signal subjected to the quadrature phase detection; a unit for obtaining third image data corresponding to the third section on the basis of the third NMR signal subjected to the phase rotation calculation; and a third display control unit for controlling the display unit so that a third sectional image corresponding to the third image data is displayed on the screen.

The unit for obtaining the first image data may include a unit for obtaining a first NMR signal corresponding to the first section and a unit for obtaining the first image data on the basis of the first NMR signal.

The unit for obtaining the second image data may include a unit for obtaining a second NMR signal corresponding to the second section, and a unit for obtaining the second image data on the basis of the second NMR signal.

DESCRIPTION OF THE PREFERRED EMBODIMENTS

Hereinafter, a magnetic resonance imaging method and apparatus according to preferred embodiments of the present invention will be explained in detail with reference to the accompanying drawings.

Figure 2:
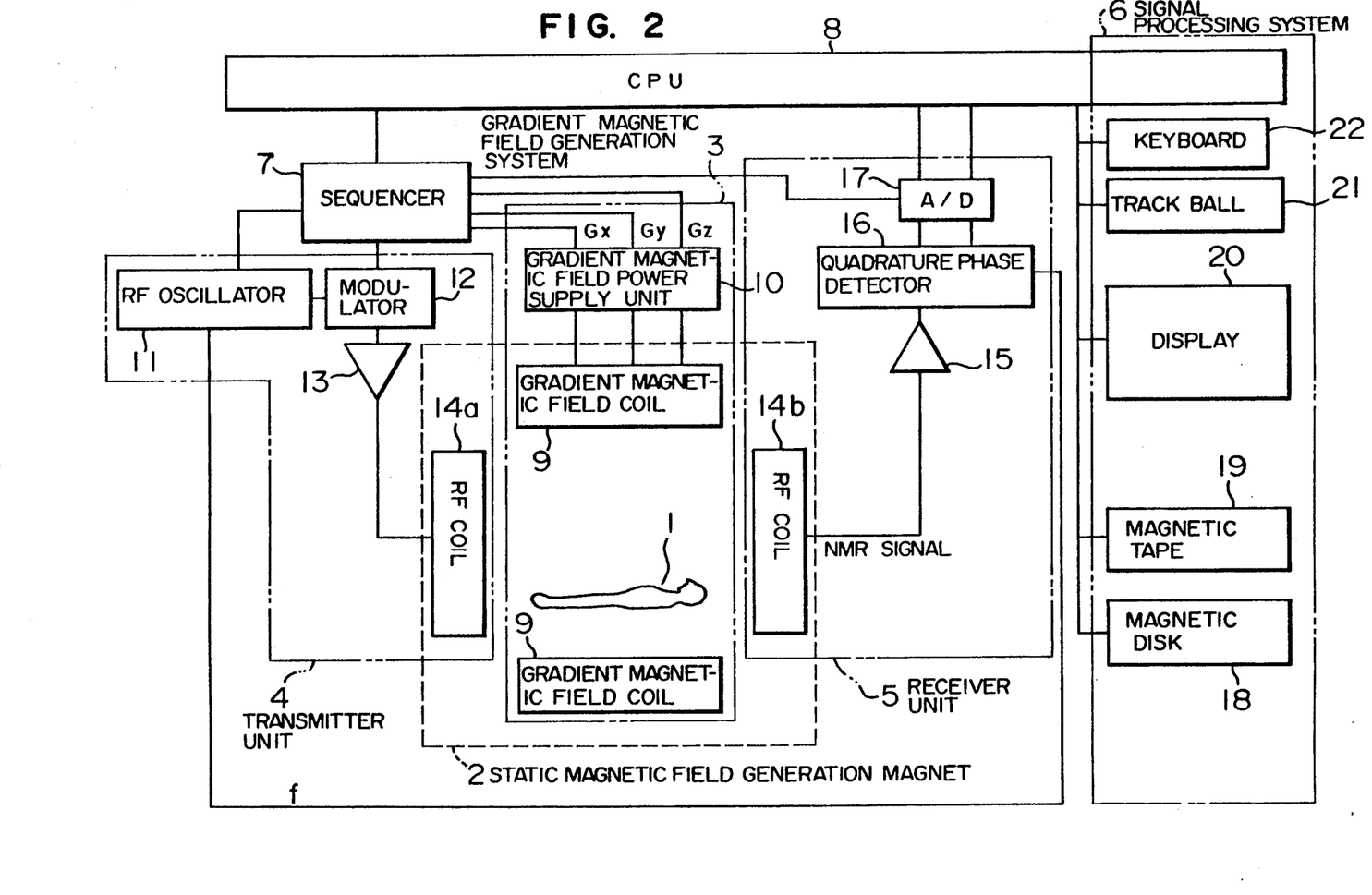
FIG. 2 is a block diagram showing the magnetic resonance imaging apparatus described above.

FIG. 2 is a schematic block diagram showing an overall structure of a magnetic resonance imaging apparatus according to an embodiment of the present invention.

The magnetic resonance imaging apparatus shown in FIG. 2 includes a static magnetic field generation system 2, a gradient magnetic field generation system 3, a transmitter unit 4, a receiver unit 5, a signal processor unit 6, a sequencer 7 and a central processing unit (CPU) 8.

The static magnetic field generation system 2 generates a homogeneous static magnetic field round an object 1 to be examined in a direction of a body axis of the object 1 or in a direction rectangular to the body axis. A magnetic field generator of a permanent magnet system or a resistive magnet system or a superconducting magnet system is disposed inside a space having a certain expansion around the object 1.

The gradient magnetic field generation system 3 comprises a gradient magnetic field coil 9 wound in directions of three axes X, Y and Z, and a gradient magnetic field power supply unit 10 for driving the respective gradient magnetic field coils. When the gradient magnetic field power supply unit 10 for the respective coil is driven in accordance with the instruction from the later-appearing sequencer 7, the gradient magnetic fields Gx, Gy and Gz in the three-axes directions X, Y, Z can be applied to the object 1. A slice plane to the object 1 can be set by the mode of application of this gradient magnetic field.

The sequencer 7 operates in such a way that an RF magnetic field pulse for causing nuclear magnetic resonance of atomic nuclei of the atoms constituting the living texture of the object 1 are repeatedly applied to the object 1 in a predetermined pulse sequence. The sequencer 7 operates under the control of the CPU 8, and sends various instructions necessary for collecting data of the tomogram (sectional image) of the object 1 to the transmitter unit 4, to the gradient magnetic field generation system 3 and to the receiver unit 5.

The transmitter unit 4 irradiates RF magnetic field pulses for causing nuclear magnetic resonance in the atomic nuclei of the atoms constituting the living texture of the object 1, by the signals sent from the sequencer 7. It comprises an RF oscillator 11, a modulator 12, an RF amplifier 12 and an RF coil 14a. The RF pulse outputted from the RF oscillator 11 is subjected to amplitude modulation by the modulator 12 in accordance with the instruction from the sequencer 7, and the RF pulse after this amplitude modulation is amplified by the RF amplifier 12 and is then supplied to an RF coil 14a disposed in the vicinity of the object 1, so that the RF magnetic field pulse (electromagnetic wave) is irradiated to the object 1.

The receiver unit 5 receives echo signals (NMR signals) emitted due to nuclear magnetic resonance of the atomic nuclei of the living texture of the object 1, and comprises an RF coil 14b, an amplifier 15, a quadrature phase detector 16 and an A/D converter 17. The responding electromagnetic wave (NMR signal) of the object 1 to the electromagnetic wave irradiated from the RF coil 14a on the transmission side is detected by the RF coil 14b disposed in the vicinity of the object 1 and is amplified by the amplifier 15. The quadrature phase detector 16 effects quadrature phase detection of this amplified NMR signal at the timing instructed by the sequencer 7, and two series of signals, i.e. a real portion and a virtual portion, are outputted from the quadrature phase detector 16. This quadrature phase detection by the quadrature phase detector 16 is carried out with a detection frequency f which is set through the sequencer 7 in accordance with the instruction from the CPU 8. In other words, the frequency (defection frequency) f of the signal applied from the RF oscilator 11 to the quadrature phase detector 16 is set through the sequencer 7 in accordance with the instruction from the CPU 8, and the quadrature phase dete4ctor 16 effects quadrature phase detection on the basis of this signal. The two-series signals outputted from the quadrature phase detector 16 are converted to digital signals by the A/D convertor, and are then sent to the signal processing unit 6.

The signal processing unit 6 comprises a storage such as a magnetic disk 18 and a magnetic tape 19, and a display 20 such as a CRT (cathode-ray tube). The CPU executes processings such as Fourier transform, image reconstruction, etc, effects suitable computation for a signal intensity distribution of the slice of the object or for a plurality of signals, converts the resulting distribution into an image, and displays it as a sectional view on the display 20.

In FIG. 2, the RF coils 14a and 14b on the transmission and reception sides, respectively, and the gradient magnetic field coil 9, are disposed inside the magnetic field space of the static magnetic field generation system 2 which is in turn disposed in the space round the object 1.

In this embodiment, the signal processing unit 6 is equipped particularly with a track ball 21 and with a keyboard 22, and the line cursor, etc, can be moved to a displayed sectional image by the operation of either one of them. When the line cursor is positioned to a predetermined position, sectional image data representative of the slice portion along the line cursor can be generated and displayed in accordance with delivery of an instruction signal.

Next, the processing steps for forming the sectional image by the CPU 8 on the basis of the operator's operation of the track ball 21 or the keyboard 22 will be explained with reference to FIG. 3.

Step S1

Figure 3:
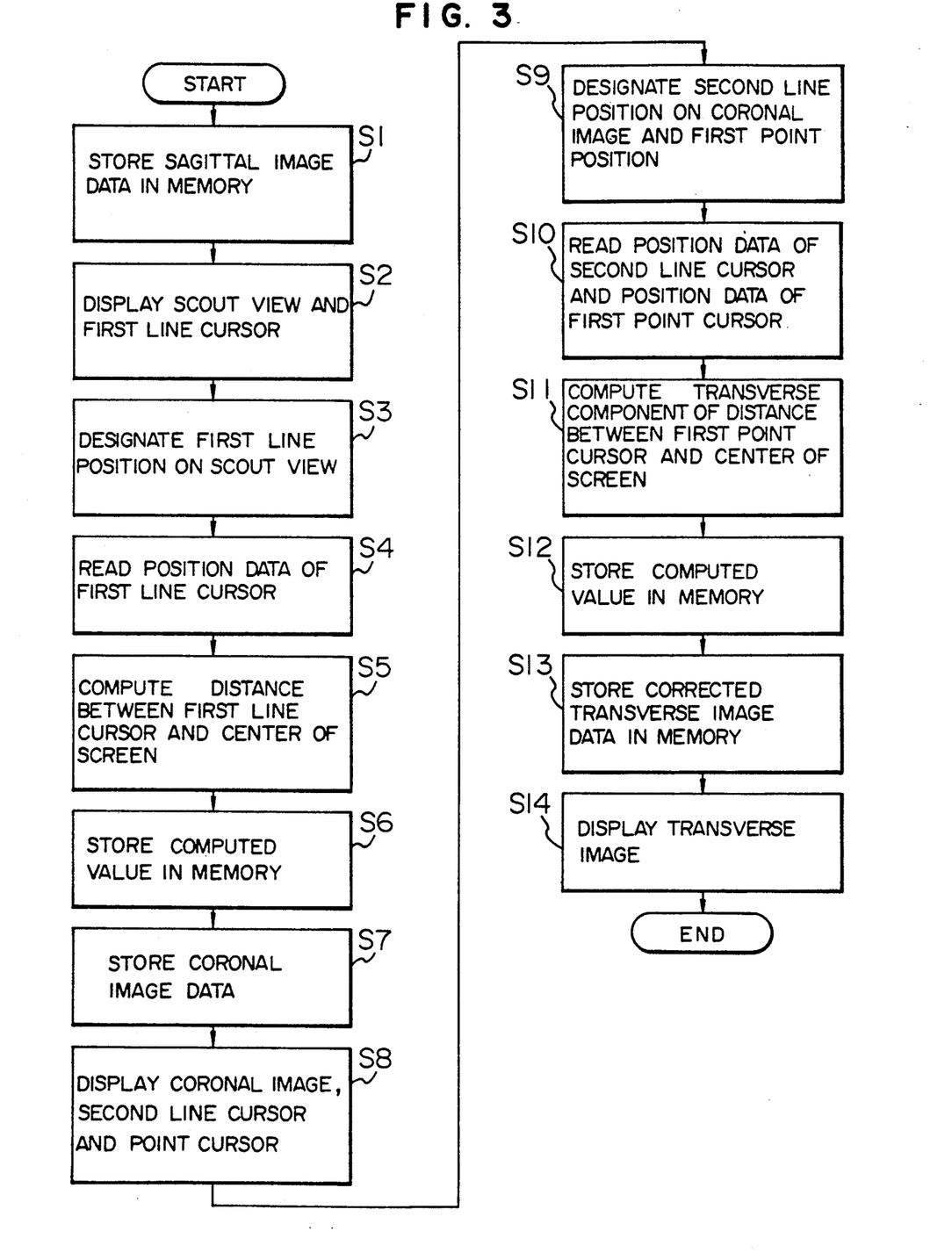
FIG. 3 is a flowchart showing an example of the operation of the magnetic resonance imaging apparatus described above.

To begin with, in the step S1 shown in FIG. 3, sagittal image data (image data corresponding to a sagittal section of the object 1) are generated in response to a start signal generated by the operation of the keyboard 22, and are then stored in the memory (magnetic disk 18 or magnetic tape 19). The image data are generated by a known method. In other words, a predetermined gradient magnetic field is applied in the gradient magnetic field generation system 3 and the RF magnetic field pulses are generated from the RF coil 14a of the transmitter unit 4. Consequently, NMR signals corresponding to the slice of the object 1 (the sagittal section as the first section in this embodiment) determined by the gradient magnetic field are detected by the RF coil 14b of the receiver unit 5. The NMR signals are amplified by the amplifier 15, and are subjected to quadrature phase detection with a predetermined detection frequency $f_1$ by the quadrature phase detector 16. Two-series signals outputted from the quadrature phase detector 16 are converted to digital signal data by the A/D converter. Processing such as Fourier transform is made for this data to generate the sagittal image data described above.

Step S2

In the next step S2, a sectional image corresponding to the sagittal section is displayed as a first sectional image on the screen of the display 20 on the basis of the sagittal image data generated in the step S1. This sectional image is a so-called "scout view". This scout view is displayed as shown in the upper column of FIG. 4, for example, and shows the object 1 inclusive of its body axis. In the upper column of FIG. 4, the left-hand portion represents the abdomen of the object 1 and the right-hand portion does the back.

Figure 4:
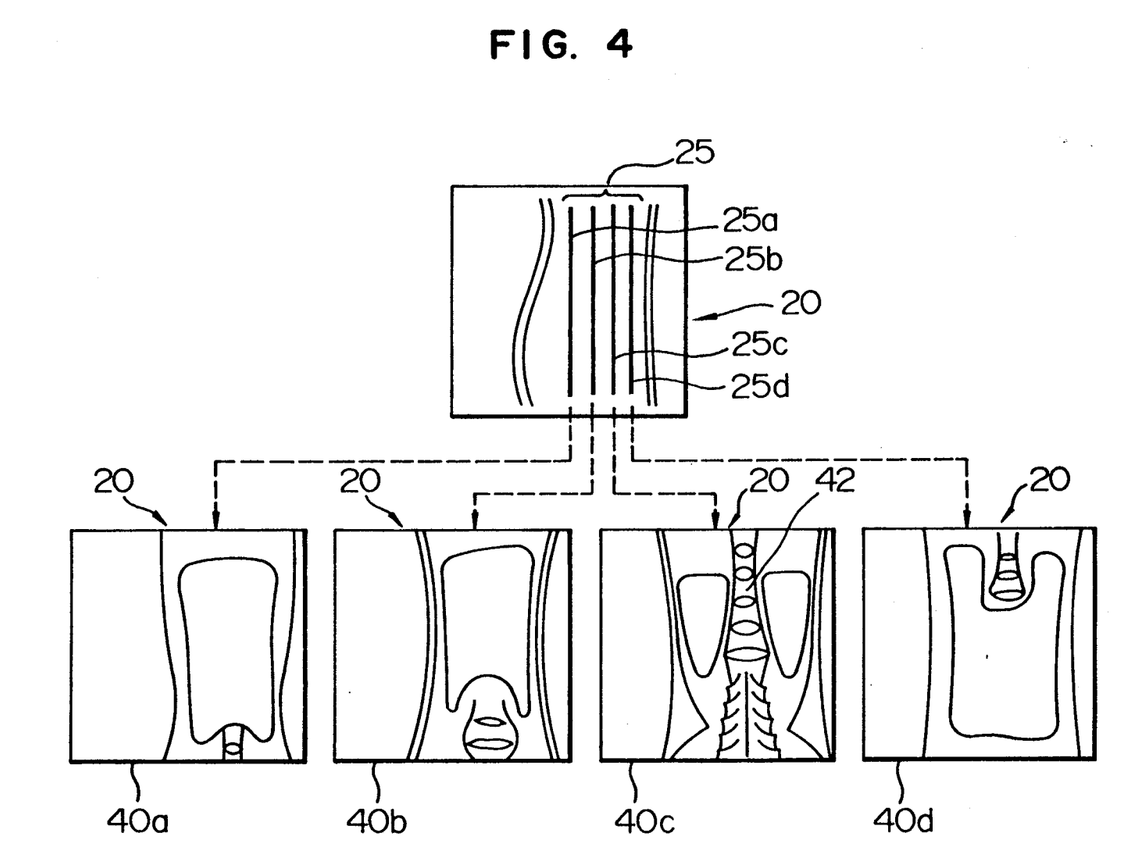
FIG. 4 shows the relationship between a first display state and a second display state on the display screen of the magnetic resonance imaging apparatus described above.

Further, in the step S2, first line cursors 25a to 25d are simultaneously displayed on the screen in super-position with the scout view. In this embodiment, the number of the first line cursors 25a to 25d are four, and these first line cursors extend in the direction of the body axis of the subject 1 (in the vertical direction of the screen described above). The first line cursors 25a to 25d can be moved in a direction rectangular to the direction of the body axis of the object 1 by the operation of the track ball 21 by the operation (in the transverse direction of the screen). By the way, only one of the line cursors 25a to 25d may be displayed.

Step S3

In the step S3, the position of a first line on the scout view is designated. In this embodiment, this designation is carried out by moving the first line cursors 25a to 25d to the respective desired positions on the scout view through the operation of the track ball 21, and then by determining the positions by the keyboard 22. Though the positions of the first line cursors 25a to 25d directly represent the first line position described above in this embodiment, the first line position may be designated by other methods without using such line cursors.

Step S4

In the step S4, data representing the determined positions of the first line cursors 25a to 25d are read, respectively.

Step S5

In the step S5, a value $y_o$ corresponding to the distance between each of the first line cursors 25a to 25d and the center of the screen is computed on the basis of the data read in the step S4. In other words, the value $y_o$ corresponding to the distance from the center of the screen to each of the first line cursors 25a to 25d in the transverse direction of the screen is computed.

Step S6

In the step S6, the values computed in the step S5 are stored in the memory.

Step S7

In the step S7, a first coronal image data corresponding to a first coronal section of the object 1 crossing rectangularly the sagittal section described above on a line on the sagittal section of the object 1 corresponding to the position of the first line cursor 25a, which is read in the step S4, is first stored in the memory. This image data, too, is generated by a known method. In other words, a gradient magnetic field (which is different from the gradient magnetic field applied in the step S1) determined on the basis of the data representing the position of the first line cursor 25a, which is read in the step S4, is applied in the gradient magnetic field generation system 3, and the RF magnetic field pulses are generated from the RF coil 14a of the transmitter unit 4. In this way, the NMR signals corresponding to the section of the object determined by the gradient magnetic field (the first coronal section) are detected by the RF coil 14b of the receiver unit 5. The NMR signals are amplified by the amplifier 15 and are then subjected to quadrature phase detection by the quadrature phase detector 16 with a predetermined detection frequency $f_1$ (which is the same as the detection frequency $f_1$ used in the step S1). The two-series signals outputted from the quadrature phase detector 16 are converted to the digital signal data by the A/D converter. Processing such as Fourier transform is executed for this data, and in this way, the first coronal image data is generated.

Further, in this step S7, the second to fourth coronal image data corresponding to the second to fourth coronal section of the object 1 crossing rectangularly the sagittal section on the lines on the sagittal section of the object 1, which correspond to the positions of the first line cursors 25a to 25d read in the step S4, respectively, are stored in the memory in the same way as described above.

Step S8

In the step S8, one coronal image, which is selected from the first to fourth coronal images 40a to 40d (refer to lower column in FIG. 4) corresponding respectively to the first to fourth coronal sections by the operation of the key board 22 on the basis of the first to fourth coronal image data generated in the step S7, is displayed on the screen as the second sectional image. The first to fourth coronal images 40a to 40d can be displayed by the operation of the keyboard 22. The following description will assume that the third coronal image 40c distinctly displaying a lumber vertebra, for example, is selected.

Figure 5A:
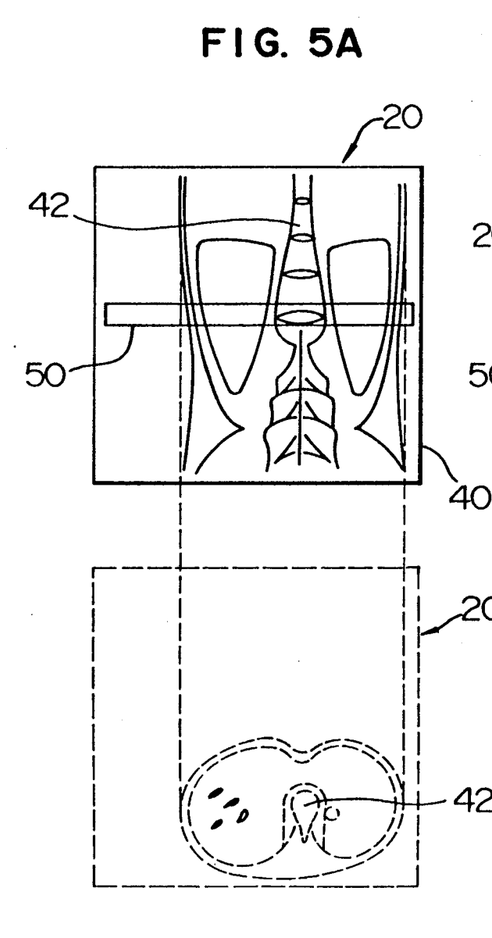
FIG. 5A shows the relationship between the second display state and a third display state on the display screen by a method which is compared with a method of the present invention.
Figure 5B:
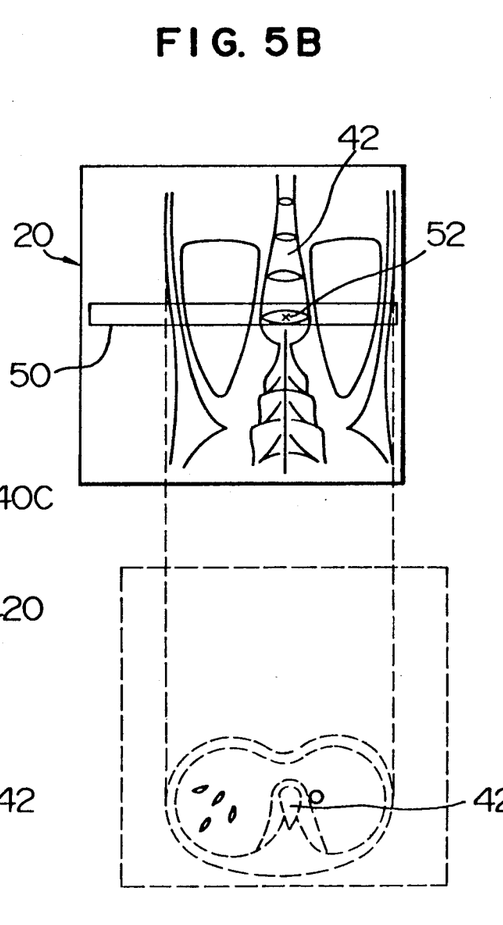
FIG. 5B shows the relationship between the second display state and the third display state on the display screen by a method which is compared with the method of the present invention.

Further, in the step S8, the second line cursor 50, which is referred to as a "box", and a point cursor 52 are simultaneously displayed on the screen in superposition with the selected coronal image 40c, as shown in the upper column of FIG. 5B. In this embodiment, the second line cursor 50 has a thickness in a vertical direction which corresponds to the slice thickness, but the first line cursor 25 need not have such a width. In this embodiment, the second line cursor 50 extends in a direction rectangular to the body axis of the object 1 (in the transverse direction of the screen). The second line cursor 50 can be moved in the direction of the body axis (in the vertical direction of the screen) by the operation of the track ball 21 by the operator. The point cursor 52 can be moved in the transverse direction of the screen along the second line cursor 50 by the operation of the track ball 21 by the operator.

Step S9

In the step S9, the position of the second line on the selected coronal image 40c and the first point contained in the position of the second line are designated. In this embodiment, designation of the second line is carried out by moving the second line cursor 50 to a desired position on the coronal image 40c by the operation of the track ball 21 and determining this position by the keyboard 22. Similarly, designation of the first point is carried out by moving the point cursor 52 to a desired position along the second line cursor 50 by the operation of the track ball 21 and determining this position by the keyboard 22. In the description which will follow, it will be assumed that the position of the lumber vertabra 42 of the object 1 is designated by the point cursor 52.

Step S10

In the step S10, data representing the position of the second line cursor 50 and data representing the position of the point cursor 52 are read, respectively.

Step S11

In the step S11, a value $x_o$ of the distance between the position of the point cursor 52 and the center of the screen, which corresponds to the component in the direction of the second line cursor 50 (in the transverse direction of the screen), is computed on the basis of the data representing the position of the point cursor 52 and read in the step S10.

Step S12

In the step S12, the value $x_o$ computed in the step S11 is stored in the memory.

Step S13

In the step S13, a transverse image data, which corresponds to a transverse section of the object 1 orthogonal to the third coronal section on the line on the third coronal section of the object corresponding to the position of the second line cursor read in the step S10, and which is corrected on the basis of the values $y_o$ and $x_o$ stored in the memory in the steps S5 and S12, is stored in the memory.

Generation of this image data is made basically by a known method, but is different from the known method in that the image data is corrected on the basis of the values $y_o$ and $x_o$.

In other words, in the gradient magnetic field generation system 3, a gradient magnetic field determined on the basis of the data representing the position of the second line cursor 50 read in the step S10 (which magnetic field is different from the gradient magnetic field applied in the steps S1 and S7) is applied, and the RF magnetic field pulses are generated from the RF coil 14a of the transmitter unit 4. Consequently, the NMR signals corresponding to the section of the object (the transverse section described above) determined by the gradient magnetic field are detected by the RF coil 14b of the receiver unit 5. The NMR signals are amplified by the amplifier 15 and are subjected to quadrature phase detection by the quadrataure phase detector with a detection frequency $f_2$ (different from the detection frequency $f_1$ used in the steps S1 and S7). This detection frequency $f_2$ is determined on the basis of the values $y_o$ and $x_o$ as will be described later. The two-siries signals outputted from the quadrature phase detector 16 are converted to the digital signal data by the A/D convertor. Phase rotation computation for rotating the phase by a later-appearing phase angle determined on the basis of the values $y_o$ and $x_o$ is effected for the NMR signals after this quadrature phase detection and A/D conversion. The corrected transverse image data described above can be obtained by executing processing such as Fourier transform for the NMR signals for which this phase rotation computation is made.

Step S14

In the step S14, the transverse image corresponding to the transverse section is displayed as the third sectional image on the screen of the display 20 on the basis of the corrected transverse image data generated in the step S13. If the detection frequency $f_2$ and the phase angle are set as will be described later on the basis of the values $y_o$ and $x_o$, the point on the transverse image corresponding to the point (the lumber vertebra 42 in this embodiment) on the transverse section specified by both the first line cursor 25c and the point cursor 52 can be displayed at the substantial center of the screen in both transverse and vertical directions as shown in FIG. 5C.

Figure 1:
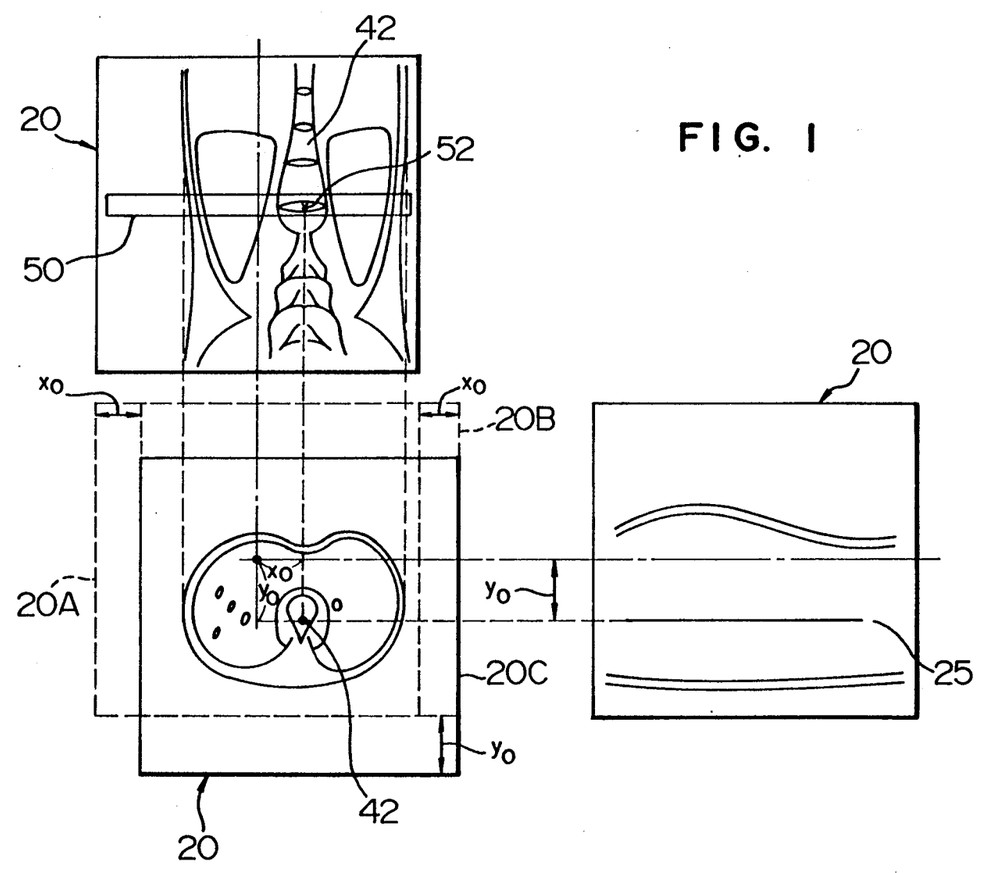
FIG. 1 shows each display state on a display screen of a magnetic resonance imaging apparatus according to an embodiment of the present invention.
Figure 5C:
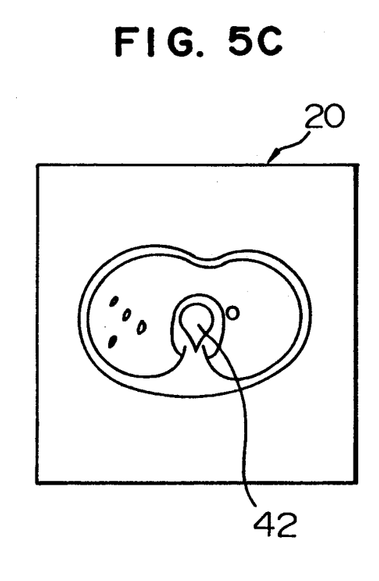
FIG. 5C shows the third display state on the display screen of the magnetic resonance imaging apparatus described above.

Incidentally, FIG. 1 shows the correlationship between the drawing in the upper column of FIG. 4, the drawing shown in the upper column of FIG. 5B and the drawing shown in FIG. 5C. The drawing shown in the upper column in FIG. 1 corresponds to the drawing shown in the upper colum of FIG. 5B, the left-hand drawing in the lower column of FIG. 1 corresponds to the drawing shown in FIG. 5C, and the right-hand drawing in the lower column of FIG. 1 corresponds to the drawing shown in the upper column of FIG. 5B. The frame 20A in FIG. 1 corresponds to the drawing in the lower column of FIG. 5A, and the frame 20B does to the diagram in the lower column in FIG. 5B which will be described later. As can be understood from FIG. 1, the frame 20B is shifted by $x_o$ in the transverse direction with respect to the frame 20A due to the position data of the point cursor 52, so that the transverse image is disposed at the center with respect to the transverse direction of the screen. The frame 20C is shifted by the distance $y_o$ of the first line cursor 25c from the center of the screen with respect to the center of the screen, so that the transverse image is disposed at the center in the vertical direction of the screen.

In this embodiment, the transverse image is the sectional image desired by the operator, and the scout view and the coronal image are displayed as a preliminary stage for obtaining the desired transverse image.

Next, the explanation will be given how the detection frequency $f_2$ and the phase angle in the step S14 are determined on the basis of the values $y_o$ and $x_o$ and why the transverse image is disposed at the center of the screen when the detection frequency $f_2$ and the phase angle are determined in such a way. The explanation will be given with reference to FIGS. 6A to 6E.

Figure 6A:
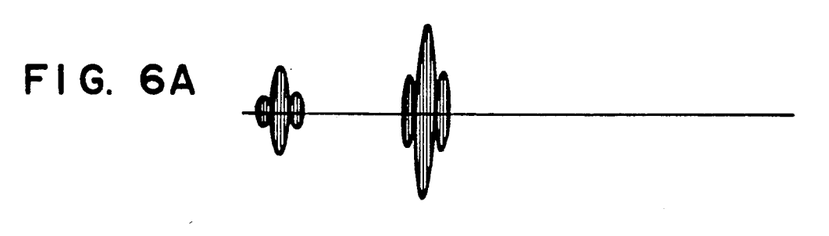
FIG. 6A shows radio frequency (RF) magnetic field pulses applied to an object to be examined.
Figure 6B:
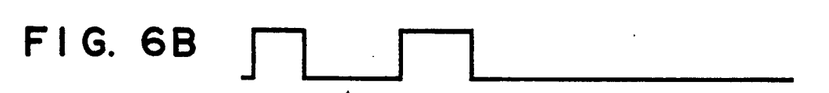
FIG. 6B shows a gradient magnetic field for slicing.
Figures 6C, 6D:
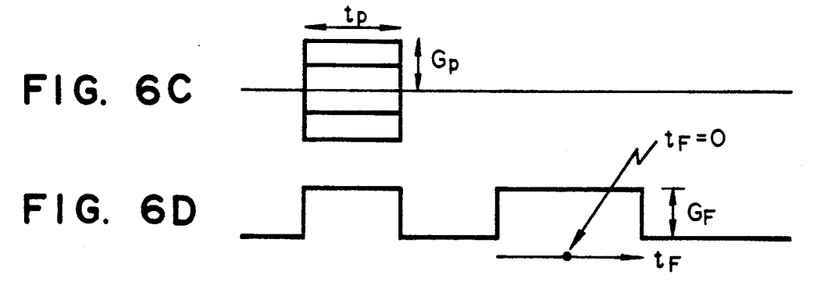
FIG. 6C shows a gradient magnetic field in a phase encoding direction.
FIG. 6D shows a gradient magnetic field in a frequency encoding direction.
Figure 6E:
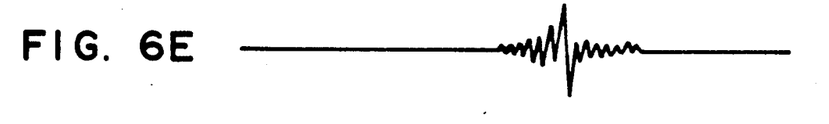
FIG. 6E shows an NMR signal.

FIGS. 6A to 6E are sequence diagrams of a spin echo method which is one of the imaging methods of the magnetic resonance imaging apparatus. By the way, the present invention is not particularly limited to the spin echo method but can employ various other imaging methods. The abscissa in FIGS. 6A to 6E represents the same time lapsed, and these diagrams show the amplitude of each signal. FIG. 6A shows the RF magnetic field pulse applied to the object 1 by the RF coil 14a. FIG. 6B shows the gradient magnetic field for slicing. FIG. 6C shows the gradient magnetic field in the phase encoding direction. FIG. 6D shows the gradient magnetic field in the frequency encoding direction. FIG. 6E shows the NMR signal received by the RF coil 14b.

Let's assume that x is the position of the image in the phase encoding direction the screen, $x_o$ is a shift distance of the position of the image in the phase encoding direction on the screen (which is the same as $x_o$ described already), y is the position of the image in the frequency encoding direction on the screen, $y_o$ is a shift distance of the image in the frequency encoding direction on the screen (which is the same as $y_o$ described already), $G_p$ is the maximum amplitude of the gradient magnetic field in the phase encoding direction (see FIG. 6C), $t_p$ is a time period of $G_p$ (see FIG. 6C), $G_F$ is the amplitude when the NMR signal of the gradient magnetic field in the frequency encoding direction is collected (see FIG. 6D), $t_F$ is the time point of $G_F$ (with the proviso that the center point of the time period of $G_F$ satisfies the relation $t_F = 0$), M is a magnetic moment of the object 1, $\gamma$ is a gyromagnetic ratio of the proton, and $H_o$ is the intensity of the static magnetic field. Then, the NMR signal S from the object 1 received by the RF coil 14b is given by the following equation (1):

$$S = \int M(x,y) e^{i\gamma[G_p \cdot x \cdot t_p + \{G_F \cdot y + H_o\} t_F]} dxdy \qquad (1)$$

When the signal S is subjected to quadrature phase detection by the quadrature phase detector 16 with the frequency $f_2$ expressed by the equation (2) below (the same frequency as the detection frequence $f_2$ described above), the signal S' after detection can be expressed by the following equation (3):

$$f_2 = \gamma(H_0 + G_F y_0) \qquad (2)$$

$$\begin{aligned} S' &= \int M(x,y) e^{i\gamma[G_p \cdot x \cdot t_p + \{G_F \cdot y + H_0\} t_F]} dxdy \cdot \\ & \quad e^{-i\gamma(H_0 + G_F y_0) \cdot t_F} \\ &= \int M(x \cdot y) e^{i\gamma[G_p \cdot x \cdot t_p + \{G_F y - y_0\} t_F]} dxdy \end{aligned} \qquad (3)$$

This signal S' is converted to the digital signal by the A/D convertor, and the digital signal is inputted to the CPU.

Next, phase rotation computation expressed by the following equation (4) for the inputted signal S', and a signal S" can be obtained.

$$S'' = S' \cdot e^{-i\gamma G_p \cdot x_0 \cdot t_p} \quad (4)$$

The following equation (5) can be obtained by substituting the equation (4) for the equation (3):

$$S'' = \int M(x,y) e^{i\gamma [G_p \cdot (x-x_0) \cdot t_p + G_F \cdot (y-y_0) \cdot t_F]} dxdy \quad (5)$$

Assuming that $X = x - x_o$ and $Y = y - y_o$, then, the equation (5) can be expressed by the following equation (6):

$$S'' = \int M(X+x_o, Y+y_o) e^{i\gamma(G_p \cdot X \cdot t_p + G_F \cdot Y \cdot t_F)} dXdY \quad (6)$$

Assuming further that $\gamma G_p t_p = K_X$, $\gamma G_F t_F = K_Y$, then, the equation (6) can be expressed by the following equation (7):

$$S'' = \int M(X+x_o, Y+y_o) e^{i(K_X \cdot X + K_Y \cdot Y)} dXdY \quad (7)$$

Next, a general Fourier transform equation is given below:

$$\begin{aligned} F(k_x, k_y) &= \int f(x,y) e^{i(k_x \cdot x + k_y \cdot y)} dxdy \\ f(x \cdot y) &= \int F(k_x, k_y) e^{-i(k_x \cdot x + k_y \cdot y)} dk_x dk_y \end{aligned} \quad (8)$$

It can be understood by comparing the equation (7) with the equation (8) that a two-dimensional distribution of the magnetic moment of the object, that is, the sectional image M $(X+x_o, Y+y_o)$, can be obtained by effecting two-dimensional Fourier transform of the equation (7). In comparison with the original sectional image M (X, Y), this sectional image M $(X+x_o, Y+y_o)$ has shifted by $x_o$ in the x direction and by $y_o$ in the y direction.

It can be appreciated from the explanation given above that if the dtection frequency $f_2$ is determined as expressed by the equation (2) in the step S13 and at the same time, when the phase rotation computation expressed by the equation (4) is conducted, the transverse image displayed in the step S14 is positioned at the center of the screen. Incidentally, the detection frequency $f_1$ used in the steps S1 and S8 may be set to $f_1 = \gamma H_o$.

In the explanation given above, the value $x_o$ as the first data corresponds to the phase encoding direction and the value $y_o$ as the second data corresponds to the frequency encoding direction. In the present invention, however, the $x_o$ value and the value $y_o$ may correspond to the frequency encoding direction and the phase encoding direction, respectively. Further, these values $x_o$ and $y_o$ need not coincide with the phse encoding direction and the frequency encoding direction. In this case, the shift distance of the component in the phase encoding direction and the shift distance of the component in the frequency encoding direction need by determined from the values $x_o$ and $y_o$, respectively.

In the embodiment given above, the point cursor 52 is displayed on the screen in the step S8 and the first point is designated in the step S9. In contrast, if the point cursor 52 is not displayed as shown in the upper colun of FIG. 5A but only the transverse image data corresponding to the transverse section of the object 1 rectangularly crossing the third coronal section of the object 1 on the line on the third coronal section, which in turn corresponds to the position of the second line cursor 50, is obtained by the same method as that of the step S1, the transverse image corresponding to the transverse section will be deviated in the transverse and vertical directions of the screen in accordance with the position of the object 1 as shown in the lower column of FIG. 5A when it is displayed on the screen on the basis of the transverse image data thus obtained.

If the phase rotation calculation is not made in the step S13, the transverse image will be deviated in the vertical direction of the screen, though it is displayed at the center in the transverse direction of the screen, as shown in the lower column of FIG. 5B.

As described above, the present invention can display a desired sectional image at the center not only in the transverse direction but also in the vertical direction of the screen, without increasing the number of sectional images that are displayed as a preliminary stage for obtaining the desired image.

The present invention is not particularly limited to the embodiment described above.

For example, though the first line cursors 25a to 25d extend in the vertical direction of the screen while the second line cursor 50 extends in the transverse direction in the embodiment given above, these line cursors 25a to 25d and 50 may be inclined.

In the embodiment given above, the first sectional image to be first displayed is the scout view, the second sectional view to be next displayed is the coronal image, and the third sectional image to be displayed last is the transverse image. However, this sequence of display may be reversed in the present invention and the scout view may be displayed as the third sectional image.

Further, in the embodiment given above, the second section of the object corresponding to the second sectional view rectangular crosses the first section of the object corresponding to the first sectional image, but the former may cross the latter at a predetermined angle other than the right angle. Similarly, though the third section of the object corresponding to the third sectional image rectangular crosses the second section of the object in the embodiment given above, they may cross at a predetermined angle other than the right angle.

We claim:

1. A magnetic resonance imaging method comprising the steps of:

displaying a first sectional image corresponding to a first section of an object to be examined on a screen of a display device;

designating a position of a first line on said first sectional image;

obtaining first data corresponding to a distance between said first line and the center of said screen;

displaying a second sectional image corresponding to a second section of said object on said screen, said second section crossing said first section on a line on said first section corresponding to the position of said first line;

designating a position of a second line on said second sectional image;

designating a position of a first point contained in the position of said second line;

obtaining second data corresponding to a component in a direction of said second line, said compornent being a component of the distance between the position of said first point and the center of said screen; and displaying a third sectional image corresponding to a third section of said object on said screen on the basis of said first and second data in such a way that a point on said third sectional image corresponding to a point of said third section is displayed at a substantial center of said screen, said third section crossing said second section on a line on said second section corresponding to the position of said second line, and the point of said third section being specified by both of said first line and said first point.

2. A magnetic resonance imaging method according to claim 1, wherein said step of displaying said first sectional image on said screen includes the steps of:

obtaining a first NMR signal corresponding to said first section;

obtaining first image data corresponding to said first section on the basis of said first NMR signal; and displaying said first sectional image on said screen on the basis of said first image data.

3. A magnetic resonance imaging method according to claim 1, wherein said step of displaying said second sectional image on said screen includes the steps of:

obtaining a second NMR signal corresponding to said second section;

obtaining second image data corresponding to said second section on the basis of said second NMR signal; and displaying said second sectional image on said screen on the basis of said second image data.

4. A magnetic resonance imaging method according to claim 1, wherein said step of displaying said third sectional image on said screen includes the steps of:

obtaining a third NMR signal corresponding to said third section of said object crossing said second section on the line on said second section corresponding to the position of said second line;

performing quadrature phase detection as to said third NMR signal with a detection frequency determined on the basis of said first and second data;

performing phase rotation comptation, for rotating a phase by a phase angle determined on the basis of said first and second data, as to said third NMR signal subjected to the quadrature phase detection;

obtaining third image data corresponding to said third section on the basis of said third NMR signal subjected to said phase rotation comptation; and displaying said third sectional image on said screen on the basis of said third image data.

5. A magnetic resonance imaging apparatus comprising:

display means, having a screen, for displaying an image on said screen;

means for obtaining first image data corresponding to a first section of an object to be examined;

first display control means for controlling said display means in such a way that a first sectional image corresponding to said first image data is displayed on said screen;

means for designating a position of a first line on said first sectional image;

means for obtaining first data corresponding to a distance between said first line and a center of said screen;

means for obtaining second image data corresponding to a second section of said object, said second section crossing said first section on a line on said first section corresponding to the position of said first line;

second display control means for controlling said display means in such a way that a first sectional image corresponding to said second image data is displayed on said screen;

means for designating a position of a second line on said second sectional image;

means for designating a position of a first point contained in the position of said second line;

means for obtaining second data corresponding to a component in a direction of sid second line said component being a component of the distance between the position of said first point and the center of said screen;

means for obtaining a third NMR signal corresponding to a third section of said object, said third section crossing said second section on a line on said second section corresponding to the position of said second line;

means for performing quadrature phase detection as to said third NMR signal with a detection frequency determined on the basis of said first and second data;

means for performing phase rotating computation, for rotating a phase by a phase angle determined on the basis of said first and second data, as to said third NMR signal subjected to said quadrature phase detection;

means for obtaining third image data corresponding to said third section on the basis of said third NMR signal subjected to said phase rotation calculation; and third display control means for controlling said display means in such a way that a third sectional image corresponding to said third image data is displayed on said screen.

6. A magnetic resonance imaging apparatus according to claim 5, wherein said means for obtaining said first image data includes:

means for obtaining a first NMR signal corresponding to said first section; and means for obtaining said first image data on the basis of said first NMR signal.

7. A magnetic resonance imaging apparatus according to claim 5, wherein said means for obtaining said second image data includes:

means for obtaining a second NMR signal corresponding to said second section; and means for obtaining said second image data on the basis of said second NMR signal.

* * * * *